United States Patent [19]

Moore

[11] Plant 4,030

[45] Mar. 29, 1977

[54] ROSE PLANT

[76] Inventor: Ralph S. Moore, 2519 E. Noble Ave., Visalia, Calif. 93277

[21] Appl. No.: 677,880

[22] Filed: Apr. 19, 1976

[51] Int. Cl.[2] ..... A01H 5/00
[52] U.S. Cl. ..... Plt./10
[58] Field of Search ..... Plt./10

*Primary Examiner*—Robert E. Bagwill

EXEMPLARY CLAIM

1. A new and distinct variety of miniature rose plant of hardy, dwarf, rounded, much branched bush type, substantially as illustrated and described, characterized by extra long lasting buds and flowers of a color similar to Fire Princess (miniature — U.S. Plant Pat. No. 3,084) and with bud and flower form similar to Eleanor (miniature — U.S. Plant Pat. No. 2,175), the general color effect being a bright shade of red (or orange red) with better than average color stability; the small buds having sepals which tend to remain against the opening buds and flowers; and further characterized by a plant which is vigorous and compact, being easy to propagate from cuttings, with small glossy to semi-glossy foliage, an abundance of bloom, with flowers borne singly or several to the stem in loose sprays or clusters.

1 Drawing Figure

1

The present invention relates to a new and distinct variety of hardy, dwarf, bush type rose plant of the miniature class; the variety being primarily characterized — as to novelty — by buds and flowers of long lasting orange red color which in general color effect is similar to Starina (miniature — U.S. Plant Pat. No. 2,646); also similar in color to Fire Princess (miniature — U.S. Plant Pat. No. 3,084) but bud is more slender.

The variety is further characterized by:

An abundance of bloom, with flowers borne singly or several to the stem in loose clusters.

Little or no fragrance.

A plant which is vigorous, of rounded spreading shape and with glossy, small foliage with pointed leaflets; the buds and flowers being similar in form and size to the variety Eleanor (miniature — U.S. Plant Pat. No. 2,175).

The plant, which has a normal height of 12 to 14 inches, can easily be maintained at lesser height by occasional trimming.

A plant which grows and blooms satisfactorily both in greenhouse and outdoors; is good for growing in pots; and provides excellent garden decoration as well as cut flowers.

The present variety of miniature rose was originated by me at my nursery located at Visalia, Calif., under conditions of careful control and observation, as an ($F_2$) seedling from a cross between Little Darling (Floribunda — U.S. Plant Pat. No. 1,581, expired) as the seed parent and Eleanor (miniature — U.S. Plant Pat. No. 2,175) as the pollen parent.

Subsequent to origination of the variety I successfully asexually reproduced it, in my nursery located as aforesaid, by budding as well as by cuttings; the reproductions having run true in all respects.

The color photograph illustrates the variety, including foliage, buds and flowers.

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy; dwarf; bush; seedling; greenhouse; outdoors; cut flowers; garden decoration; potted plant.

2

Class: Miniature. Name of present variety: 'Christine Weinert'.

Flowers:

*Continuity.*—Continuous — repeat bloom all season.

*Fragrance.*—little or none.

Flowers borne: Singly and several together (3 to 5) on slender wiry, short stems.

Quantity of bloom: Abundant both outside and in greenhouse.

Bud: Peduncle — medium length; slender but sturdy; erect; medium green, sometimes tinted bronze; hairs — usually none. Before calyx breaks — size — small; form long; pointed with foliaceous appendages and numerous short hairs on surface of bud; with foliaceous parts extending beyond the tip of the bud equal to one-half or more of its length. Color — medium green, occasionally tinted with bronze. As calyx breaks, color — orange red. As first petal opens — same general color: size — small.

Bloom: Size when fully open — small, averaging about 30–35 mm. Petalage — double — 20–25 petals, arranged regularly plus sometimes several small petaloids. Form — cupped at first, becoming higher in the center, with petals rolled loosely outward, and later at maturity rounded with petals rolled loosely outward and downward.

Petals: Quite thick; satiny on inside and satiny on outside. Shape — Outside petals, broad lanceolate (nearly round) with acute or rounded tip; intermediate — broad lanceolate (nearly oval) with acute or rounded tip; inside — lanceolate with acute tip.

Color: Newly opened flower from a plant grown in plastic greenhouse (March, 1976), Visalia, Calif.

*Outside Petal.*—Outside surface — near Geranium Lake 20/1 with small near white area at base; inside surface — near Vermilion 18 with small near white area at base.

*Intermediate Petal.*—Outside surface — same as intermediate petal; inside surface — same as intermediate petal.

*Inner Petal.*—Outside surface — same as intermediate petal; inside surface — same as intermediate petal. General color effect newly opened flowers — bright orangy red, similar to Fire Princess. Three days open — color similar to newly opened flower. Behavior — as flowers age petals may become darker shade before dropping off. In warmer weather and high light intensity the red color may be lighter and the orange undertone is less pronounced. Spent petals may persist for a time. Flower longevity (October, 1975) — plant in pot 8–10 days or longer. Cut flowers at living room temperature 5–7 days or longer.

Reproductive Organs:

*Stamens.*—Abundant, arranged regularly about pistil.

*Filaments.*—Short, yellow.

*Anthers.*—Well formed; yellow.

*Pollen.*—Little or none.

*Pistils.*—Average number.

*Styles.*—Fairly even; short; bunched; color — near white.

*Stigma.*—Nearly white.

*Hips.*—None.

*Sepals.*—Permanent; spear shaped; flat or may point (curve) upward.

*Seeds.*—None.

*Ovaries.*—All enclosed in calyx.

Foliage:

*Leaves.*—Compound of five (sometimes three) leaflets; abundant; small; leathery; glossy.

*Leaflets.*—Shape: Broad, nearly oval; apex acute; base rounded or rounded acute. Margin serrate (usually deeper than normal). Color: normal green; new growth — normal (medium) green. Rachis: medium strength; upper side may have several tiny short prickles, grooved; underside sparsely thorny with few or no tiny prickles. Stipules: medium long; medium width with hairy or serrated edges; medium length narrow points which turn out at more or less than 45°.

Growth:

*Habit.*—Dwarf; bushy; rounded; much branched.

*Growth.*—Free vigorous; internodes short.

*Canes.*—Medium; slender; sturdy.

*Main stems.*—Color — dull green. Thorns — sparsely thorny; small; hooked slightly downwards; color — brown. Prickles — none. Hairs — none.

*Branches.*—Color — medium green. Thorns — moderately thorny. Short length; slender; hooked slightly downward. Medium to short oval base. Prickles — none. Hairs — none.

*New shoots.*—Color — medium green; thorns — moderate; medium length; hooked slightly downward, reddish color; sharp points; base oval. Prickles — none. Hairs — none.

The miniature rose plant and its flowers as herein described may vary in slight detail due to climatic, soil and cultural conditions under which the variety may be grown; the present description being of the variety as grown at Visalia, Calif.

The following is claimed:

1. A new and distinct variety of miniature rose plant of hardy, dwarf, rounded, much branched bush type, substantially as illustrated and described, characterized by extra long lasting buds and flowers of a color similar to Fire Princess (miniature — U.S. Plant Pat. No. 3,084) and with bud and flower form similar to Eleanor (miniature — U.S. Plant Pat. No. 2,175), the general color effect being a bright shade of red (or orange red) with better than average color stability; the small buds having sepals which tend to remain against the opening buds and flowers; and further characterized by a plant which is vigorous and compact, being easy to propagate from cuttings, with small glossy to semi-glossy foliage, an abundance of bloom, with flowers borne singly or several to the stem in loose sprays or clusters.

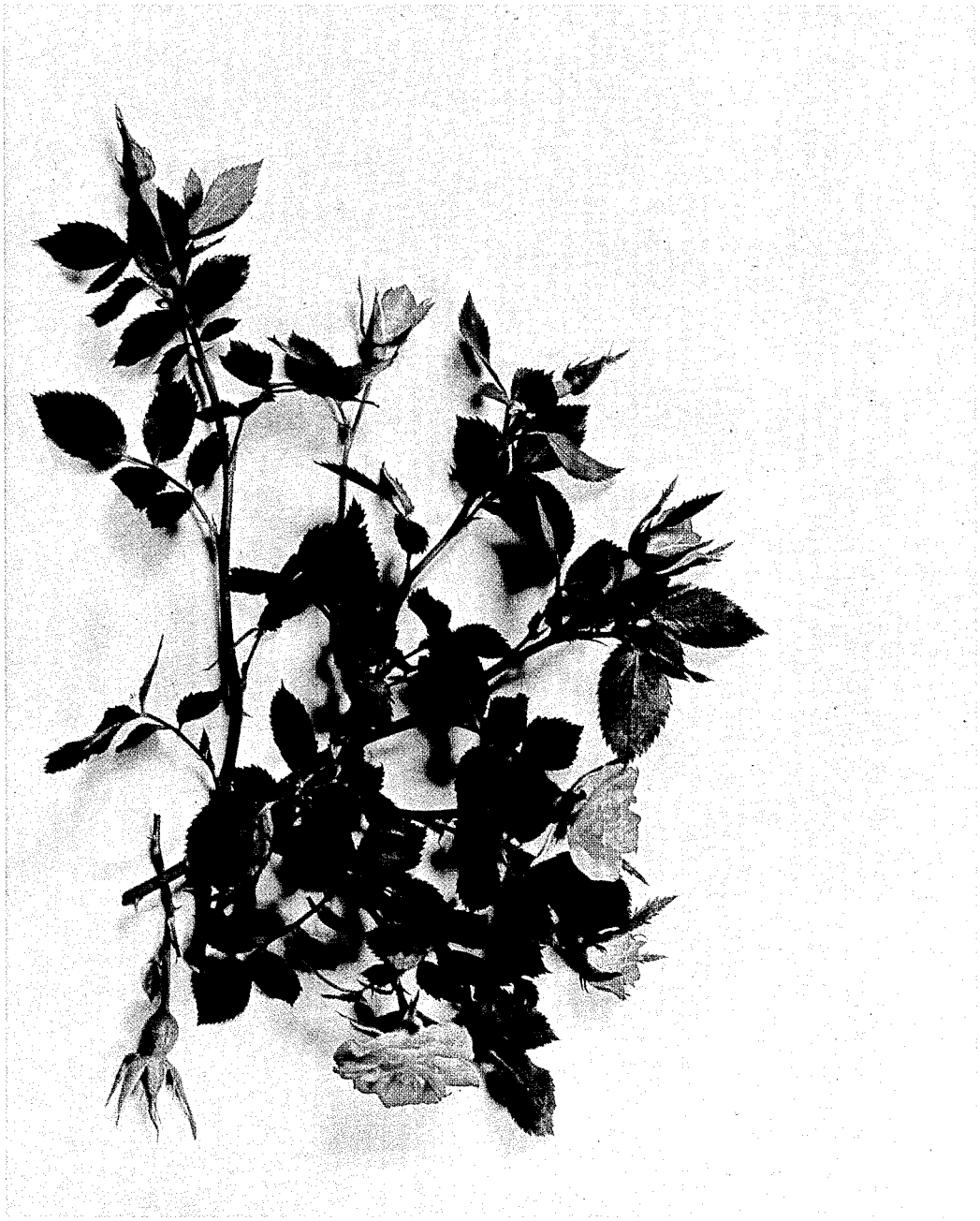

* * * * *